US006985223B2

(12) United States Patent
Drachev et al.

(10) Patent No.: US 6,985,223 B2
(45) Date of Patent: Jan. 10, 2006

(54) RAMAN IMAGING AND SENSING APPARATUS EMPLOYING NANOANTENNAS

(75) Inventors: Vladimir P. Drachev, West Lafayette, IN (US); Vladimir M. Shalaev, West Lafayette, IN (US); Andrey K. Sarychev, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 19 days.

(21) Appl. No.: 10/753,155

(22) Filed: Jan. 6, 2004

(65) Prior Publication Data
US 2004/0174521 A1 Sep. 9, 2004

Related U.S. Application Data

(60) Provisional application No. 60/453,107, filed on Mar. 7, 2003.

(51) Int. Cl.
*G01J 3/44* (2006.01)

(52) U.S. Cl. ...................................................... 356/301
(58) Field of Classification Search ................. 356/301
See application file for complete search history.

(56) References Cited

U.S. PATENT DOCUMENTS

| 5,362,653 A | | 11/1994 | Carr et al. |
| 5,479,024 A | * | 12/1995 | Hillner et al. ........... 350/458.1 |
| 5,534,997 A | | 7/1996 | Schrader |
| 6,002,471 A | * | 12/1999 | Quake ........................ 356/301 |
| 6,144,028 A | | 11/2000 | Kley |
| 6,265,711 B1 | | 7/2001 | Kley |
| 6,337,479 B1 | | 1/2002 | Kley |
| 6,483,581 B1 | | 11/2002 | Ben-Amotz et al. |
| 6,643,012 B2 | | 11/2003 | Shen et al. |
| 6,835,926 B2 | * | 12/2004 | Weitekamp et al. ......... 250/234 |
| 6,850,323 B2 | * | 2/2005 | Anderson ................... 356/301 |
| 2002/0105641 A1 | | 8/2002 | Anderson |
| 2003/0203502 A1 | * | 10/2003 | Zenhausern et al. ........ 356/300 |
| 2003/0231304 A1 | * | 12/2003 | Chan et al. ................. 356/301 |
| 2004/0161750 A1 | * | 8/2004 | Sun et al. ....................... 435/6 |

FOREIGN PATENT DOCUMENTS

DE 102 17 948 A1 * 11/2003

OTHER PUBLICATIONS

Ann E. Grow, Laurie L. Wood, Johanna L. Claycomb, Peggy A Thompson, "New biochip technology for label-free detection of pathogens and their toxins", Journal of Microbiological Methods 53 (2003), pp. 221-233.

S. Webster, D.A. Smith, D.N. Batchelder, "Raman microscopy using a scanning near-field optical probe", Vibrational Spectroscopy 18 (1998), pp. 51-59.

(Continued)

*Primary Examiner*—F. L. Evans
*Assistant Examiner*—Kara Geisel
(74) *Attorney, Agent, or Firm*—Brinks Hofer Gilson Lione

(57) ABSTRACT

A Raman imaging and sensing apparatus is described. The apparatus employs a nanoantenna structure which includes a metal tip spaced from a metal surface or particle. A light beam impinges upon the nanoantenna and causes plasmon resonance. The plasmon resonance excites a sample resulting in dramatically enhanced Raman scattering of the sample. The Raman scatter is collected by a spectrophotometer which provides an output signal indicative of the composition of the sample.

21 Claims, 6 Drawing Sheets

OTHER PUBLICATIONS

E.J. Ayers, H.D. Hallen, "Surface enhancement in near-field Raman spectroscopy", Applied Physics Letters, vol. 76, No. 26, Jun. 26, 2000, pp. 3911-3913.

C.L. Jahncke, M.A. Paesler, H.D. Hallen, "Raman imaging with near-field scanning optical microscopy", Appl. Phys. Letter. 67 (17), Oct. 23, 1995, pp. 2483-2485.

S.G. Rautian, V.P. Safonov, P.A. Chubakov, V.M. Shalaev, M.I. Shtokman, "Surface-enhanced parametric scattering of light by silver clusters", Pis'maZh.Eksp. Teor.Fiz. 47, No. 4, Feb. 25, 1988, pp. 200-203.

F. Brouers S. Blacher, A.N. Lagarkov, Andrey K. Sarychev, Parice Gadenne, Vladimir M. Shalaev, "Theory of giant Raman scattering from semicontinuous metal films", Physical Review B. vol. 55, No. 19, May 15, 1997-I, pp. 234-245, 275.

F.J. Garcia-Vidal, J.B. Pendry, "Collective Theory for Surface Enhanced Raman Scattering", Physical Review Letters, vol. 77, No. 6, Aug. 5, 1996, pp. 1163-1166.

Hongxing Xu, Erik J. Bjerneld, K.V.G.K. Murty, Charbel Tengroth, Mikael Kall, "Surface Enhanced Raman Scattering" Condensed Matter Physics, one page.

Katrin Kneipp, Yang, Wang, Harald Kneipp, Lev T. Perelman, Irving Itzkan, Ramachandra R. Dasari, Michael S. Feld, Single Molecule Detection Using Surface-Enhanced Raman Scattering (SERS), Physical Review Letters,, vol. 78, No. 9, Mar. 3, 1997, pp. 1667-1670.

Raoul M. Stöckle, Yung Doug Suh, Volker Deckert, Renato Zenobi, "Nanoscale chemical analysis by tip-enhanced Raman spectroscopy", Chemical Physical Letters 318 (2000), pp. 131-136.

Vladimir M. Shalaev, "Nonlinear Optics of Random Media", Springer Tracts in Modern Physics, vol. 158, pp. 1-147.

Andrey K. Sarychev, Vladimir M. Shalaev, "Electromagnetic field fluctuations and optical nonlinearities in metal-dielectric composites", Physics Reports 335 (2000), pp. 275-371.

Yasushi Inouye and Satoshi Kawata, "Near-field scanning optical microscope with a metallic probe tip," *Optics Letters*, Feb. 1, 1994, vol. 19, No. 3, Osaka, Japan.

* cited by examiner

RAMAN IMAGING AND SENSING APPARATUS EMPLOYING NANOANTENNAS

RELATED APPLICATION

This application claims priority to U.S. Provisional Application Ser. No. 60/453,107 filed Mar. 7, 2003.

BRIEF DESCRIPTION OF THE INVENTION

The present invention relates generally to a Raman imaging and sensing apparatus and more particularly to such apparatus which employs metal tip-substrate nanoantennas for Raman imaging and sensing of atoms, molecules, ions, etc.

BACKGROUND OF THE INVENTION

Raman spectroscopy measures molecular vibrations, which are determined by the structure and chemical bonding as well as the masses of constituent atoms, molecules, ions, etc. Raman spectra provide us with unique chemical and structural identification. Conventional micro-Raman spectroscopy has a spatial resolution of about 0.5 µm governed by the diffraction limit and even worse for IR spectrometers because of the longer wavelengths. The near-field scanning Raman microscopy (NSRM) exploits an optical fiber tip with a small aperture to deliver laser radiation or collect the scattered light [S. Webster et al., *Vibrat. Spectrosc.* 18 (1998) 51; E. J. Ayars and H. D. Hallen, *Appl. Phys. Lett.* 76 (2000) 3911; C. Jahncke et al., *Appl. Phys. Lett.* 67 (1995) 2483]. The main reason for limited use of NSRM stems from the facts that Raman signals are intrinsically weak because very low laser power can be delivered through a fiber tip (typically, $10^{-7}$ W). Another serious drawback of a fiber based delivery or collection systems are parasitic Raman signal resulting from the fiber itself.

An alternative approach to the one based on the use of optical fiber tips is to use apertureless metal tip-mediated SERS which improves significantly the Raman intensity [R. M. Stockle et al., *Chem. Phys. Lett.* 318 (2000) 131; M. S. Anderson, U.S. patent, Pub. No.: U.S. 2002/0105641 A1; S. Kawata and Y. Inouye, Jpn. Patent No. 3190945 (filed 1992/registered 2001; Y. Inouye and S. Kawata, Opt. Lett., vol. 19, 159 (1994)]. However, the enhancement factor is several orders of magnitude less than the enhancement for SERS in conventional SERS-active substrates (colloid aggregates, electrochemically etched metal surfaces, etc.), and it is restricted by a low quality factor of the plasmon resonance for a single particle (metal tip) used in this approach. The enhancement occurs only within a narrow spectral range.

OBJECTS AND SUMMARY OF THE INVENTION

The present invention enables one to combine the advantages of high sensitivity of surface-enhanced Raman scattering (SERS) with sub-wavelength spatial resolution of near-field scanning optical microscope (NSOM) and nanometer resolution of atomic force microscope (AFM). The invention also facilitates nanoscale measurements of vibration spectra of molecules and their Raman and topographical imaging. The metal tip-substrate nanoantenna (MTSN) described herein makes possible single-molecule detection along with sub-wavelength imaging. It provides a new powerful tool for protein detection, drug discovery, and nanoscale chemical analysis, which are compatible with conventional scanning probe microscopy (SPM), AFM, and NSOM. The metal-tip substrate-based sensor allows a molecule counting approach instead of the intensity measurement approach. It provides a new way for ultra-low level of molecular concentration detection and analysis.

Metal tip-substrate nanoantennas (MTSN) are disclosed which significantly increase the surface enhanced Raman scattering (SERS) as compared to the SERS for a single particle or tip. The Raman imaging and sensing apparatus includes a metal tip (or metal-coated tip) which is spaced from a metal surface or metal particle on a dielectric surface to form therewith a nanoantenna and a light source for causing plasmon resonance between the metal tip and the spaced metal surface or metal particles. The plasmon resonance is coupled to a sample which generates a characteristic Raman signal. The apparatus can include a system such as that used in atomic force microscopes for precisely locating the tip relative to the surface or particles on the surface and for scanning the surface. A microscope such as a near field microscope can be used to receive the light scattered by the atoms, molecules, etc. (Raman scatter). A spectrophotometer provides a display of Raman signal intensity as a function of wavelength for the sample molecules, atoms, ions, etc. which are coupled to and enhanced by the plasmon resonance.

It is therefore an object of the present invention to provide an apparatus for increasing surface enhanced Raman scattering.

It is another object of the present invention to provide a Raman imaging and sensing apparatus employing nanoantennas.

It is a further object of the present invention to provide a Raman imaging and sensing apparatus which includes a source of optical radiation and a Raman spectrophotometer for collecting Raman scattering at a nanoantenna position and analyzing such radiation. The apparatus may include means for scanning the nanoantenna position.

There is provided an apparatus for exciting Raman scatter at the molecular level including an antenna formed by a metal tip spaced from a metal surface or metal particle and a light source for projecting a light beam onto the nanoantenna to cause plasmon resonance for enhanced exciting molecules and causing nanoantenna-enhanced Raman scattering.

There is provided an apparatus of the above type including optics for collecting and analyzing the radiation which may also include means for scanning a sample to obtain data from a number of the same or different individual molecules, atoms, ions, etc.

BRIEF DESCRIPTION OF THE DRAWINGS

The invention will be more clearly understood from the following description when read in conjunction with the accompanying drawings of which.

DESCRIPTION OF PREFERRED EMBODIMENTS

In accordance with the present invention plasmon resonance is induced by light striking a nanoantenna which comprises a metal tip and a metal substrate or particle spaced from the tip with the plasmon resonance exciting a sample at the interface to cause molecular vibrations which provide Raman scattering.

Let us estimate the advantage of using a nanoantenna instead of a single particle or tip as in the prior art SERS. One can consider the simplest nanoantenna as a pair of metal particles for this purpose. The electric field of a resonant light wave acting inside the pair is stronger than the local field in a single particle. The enhancement factors $E_i/E_0$ for a local field $E_i$, in comparison with an incident field $E_0$, is $G = \epsilon_1^2/3\epsilon_2$ for a plasmon resonance in a pair [S. G. Rautian et al., *JETP Lett.* 47 (1988) 243] and $f_1 = 3\epsilon_0/i\epsilon_2$ for a single particle. Here $\epsilon = \epsilon_0 \epsilon_1 + i\epsilon_2$ and $\epsilon_0$ are the dielectric constants of a metal particle and a host medium. A value of G=18 is estimated for a pair of silver particles at wavelength of about 532 nm, and in the near infrared (IR) it can be as high as $10^2$ to $10^3$ The maximum value of $|f_1|$ is equal 2 for a single particle at the surface plasmon resonance (400 nm). Since surface enhanced Raman signal is proportional to the $4^{th}$ power of the field one can get a factor of about $10^4$ increase in SERS for a pair with respect to a single particle in the visible spectral range and even more in the near IR, up to $10^{12}$. Note that the enhancement factor is particle-shape dependent for both cases and can be calculated numerically.

In accordance with one embodiment of the present invention, engineered nanoantennas are used to achieve the maximal enhancement of Raman scattering from nanoscale size areas governed by tip positioning. The nanoantennas are specially designed plasmonic structures that act as "smart" optical nanoantennas focusing electromagnetic energy on nanometer scale areas, with high spatial and spectral control of the energy concentration. These nanoantennas are capable of strong enhancement of a number of optical phenomena, such as the extraordinary optical transmittance, Raman scattering, nonlinear photoluminescence, Kerr optical non-linearity, and many other important optical effects. An optical nanoantenna typically consists of two shaped metal nanostructures (e.g., particles) placed at a certain distance from each other (on the order of few to tens nanometers). This distance between the two parts forming the nanoantenna (metal tip and metal particle or metal surface) can be precisely controlled in apparatuses based on atomic force microscope or near-field scanning optical microscope.

Figure 1:
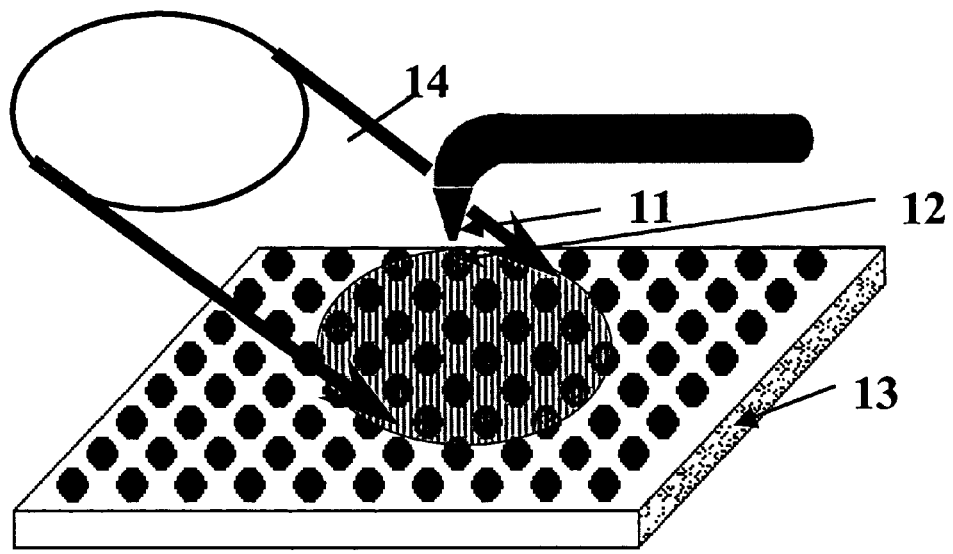
FIG. 1 shows a nanoantenna including a tip and spaced particles.

Referring to FIG. 1, the metal tip-substrate nanoantenna consists of a metallic) metal or metallized) tip 11, as the first part of the nanoantenna, and a metal particle 12 placed on the substrate 13 as the second part of the nanoantenna. When the two nanostructures are in close proximity to each other they form a resonating, antenna-like structure which is excited into plasmon resonance by an impinging light beam 14, such as a laser beam. The plasmon resonance is coupled to a sample and vibrates the sample molecules, atoms, ions, etc., and a characteristic Raman scatter (optical signal) is generated. An array of particles 12 placed on the substrate are preferable to use so that the second part of the nanoantenna is distributed over the surface in any desired position. Each tip-substrate particle pair can support plasmon modes with high quality factors, resulting in high local-field enhancement in the controlled gaps between the two parts of the nanoantennas. This enhancement can be far greater than the enhancement one can typically obtain for a single particle, such as in the case of near-field scanning Raman microscopy. The nanoantenna enhancement depends on particle shapes, the distance between the particles, and laser frequency and polarization. Thus this approach realizes, simultaneously, very large spatial and polarization-frequency selectivity in molecule sensing. We note that for such detection various optical phenomena (both linear and nonlinear) can be employed, such as SERS, hyper-Raman scattering, photoluminescence, and multi-photon pumped luminescence.

The nanoantenna also allows one to control the sensing and its resolution by varying the spacing of the nanoparticles or the particle tip spacing. An advantage of nanoantennas is the ability to control tip-particle distance to meet the resonance condition for nanoantenna excitation at various optical frequencies. The large enhancement and the excellent frequency, polarization, and space control of the detection makes it possible to achieve high signals with unparalleled spatial resolution in molecule detection. A conventional SPM (including atomic force microscope (AFM) and near-field scanning optical microscope (NSOM) can be used to control the positioning of the tip. Feedback allows the control of the spacing between the two parts of the nanoantennas. The use of, for example, tuning fork feedback (tapping mode) provides the modulation of SERS signal, making possible the detection at the modulation frequency, further increasing of the spatial resolution. Molecules of interest can be deposited on the substrate and then probed by scanning the tip from one particle or position to the next. Note that the MTSN can be a powerful SERS sensor and it can be employed with other intermolecular force measurements using a functionalized tip.

Figure 2:
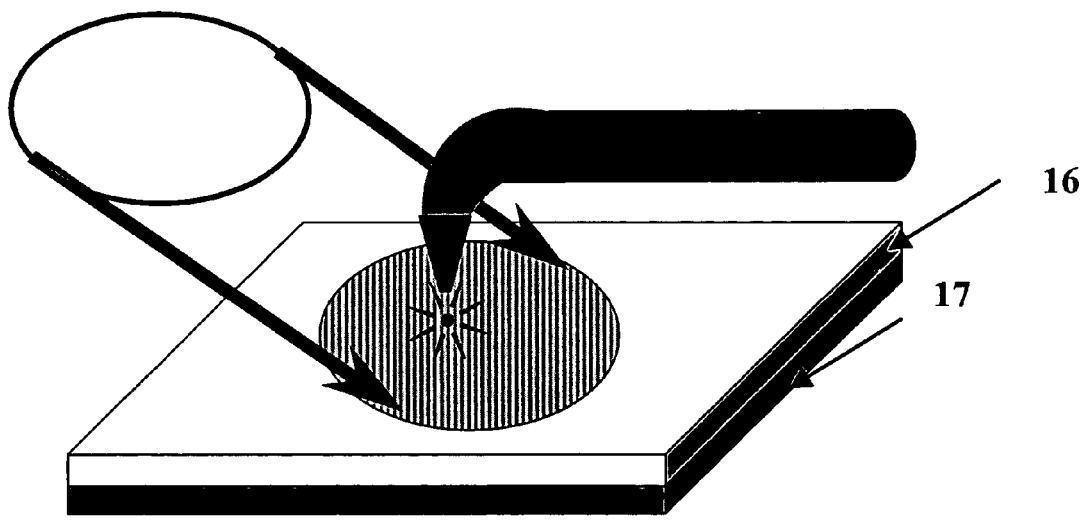
FIG. 2 shows a nanoantenna including a tip and a spaced metal surface or film.

A flat metal film 16 on a dielectric substrate 17, FIG. 2, can be used as the second part of the nanoantenna. As the tip 11 approaches the metal film 16 its (quasi-)electrostatic image is formed establishing the two parts needed for nanoantenna enhanced molecular sensing. As herein described the metal-tip substrate nanoantenna refers to a metal-tip-particle antenna or a metal-tip-metal film antenna.

The proposed MTSN sensing assumes all possible illumination/collection modes: transmission, reflection, and excitation by the evanescent wave. In the last case, the substrate should be placed on the hypotenuse plane of a prism.

The MTSN sensing opens a unique feasibility for biomolecule quantitative analysis since the nanoantenna SERS sensitivity allows one to detect single molecules, with lateral resolution which is comparable to a typical biomolecule size. Molecule counting (MC) assumes the use of a discriminator software module to distinguish spatial peaks on spectral fingerprints of a molecule. An estimate shows that molecule counting has a potential to provide a unique dynamic range on the order of $10^6$–$10^7$ for ultra-low concentration measurements.

Figure 3:
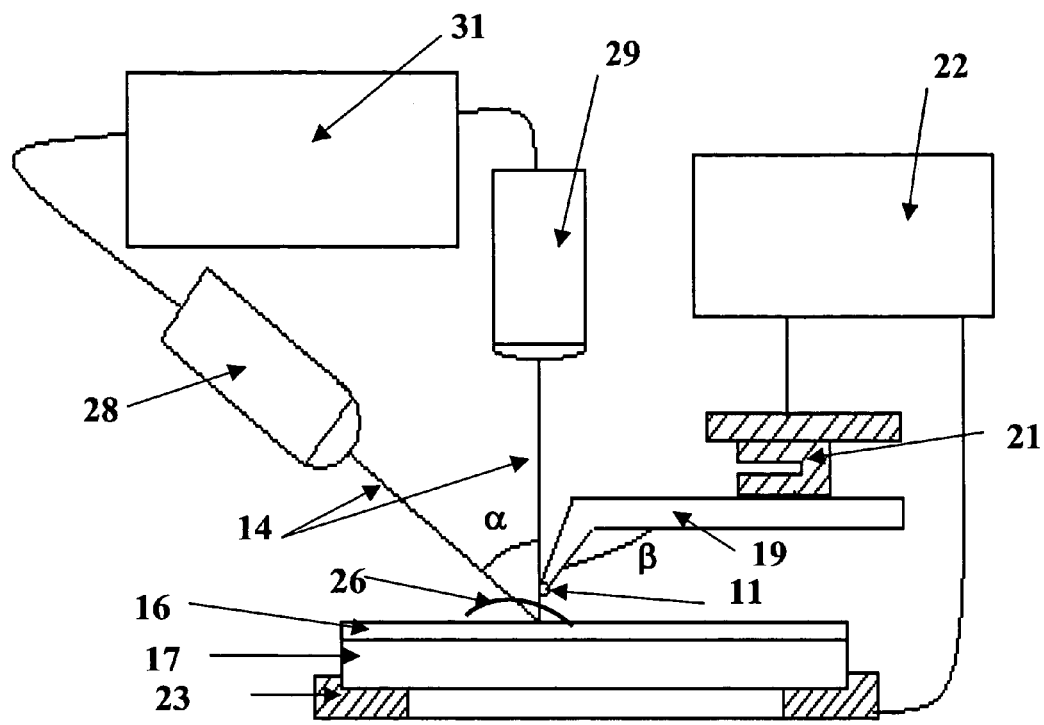
FIG. 3 is a schematic diagram of a Raman imaging and sensing apparatus in accordance with one embodiment of the present invention.

A suitable apparatus for Raman imaging and sensing is schematically illustrated in FIG. 3. The apparatus comprises a nanoantenna probe 19 including a metal tip 11 which cooperates with the metal film 16 carried by dielectric base 17. The tip 11 is attached to the scanning probe mount 21 of a scanning probe atomic force microscope which includes conventional control circuits 22. The substrate 17 is carried on a scanner platform 23 also coupled to the control circuit 22. The control circuit 22 includes feedback which provides control of the tip-substrate distance. The tip may be a metal probe such as that used in an atomic force microscope, or it may be a dielectric probe with metal on its tip, or a dielectric probe covered with a metal particle aggregate. The metal film 16 comprises a periodic or quasi-periodic metal particle array or a continuous metal layer fabricated on the dielectric base 17. The sample 26 is placed on the metal film. The sample in the space between the metal tip and metal is excited by the plasmon resonance of the nanoantenna and generates Raman scatter. It is to be understood that in the case of a two- or multi-component sample the sample can be deposited on both the tip and substrate. The dielectric substrate may include metal particles or regions which can be formed by photolithography in precise patterns The scanning probe microscope can be an atomic force microscope or other device providing x,y,z positioning of the tip The Raman spectrophotometer includes means for projecting a light beam to excite plasmon resonance and optics for receiving Raman scattered radiation and analyzing the radiation to identify the sample. Thus, the spectrophotometer 31 includes a laser or other quasi-monochromatic light source, a monochromator and photodetector (for example CCD camera), and also illuminating optics 28 and collector optics 29 providing spectral analysis of the Raman or luminescent signals collected by the optics. The Raman spectrometer is optically coupled to the tip substrate nanoantenna and the scanning probe microscope, and the nanoantenna is electrically coupled to the scanner. It is to be understood the illuminating/collection optics can be combined in one device, for example a confocal microscope in the backscattering geometry or have two separate optical axes as illustrated with arbitrary angle $\alpha$ between them. An evanescent mode of illumination can be employed.

The key issue of the tip substrate antenna is to provide a condition for exclusive excitation of plasmon resonance at the tip position with insufficient excitation over the rest of the substrate area. To address this issue the particle array spacing on the substrate and the tip substrate distance, the polarization and the wavelength of illumining laser beam are self-consistent. The controlled tip substrate nanoantenna provides a fine adjustment for nanoantenna resonance at the tip position for a chosen wavelength. Wavelength and/or particle array spacing are chosen out of the need of plasmon resonance of the nanoantenna structure. Polarization selectively provides additional support for exclusive excitation since the preferred direction for substrate structure and for tip-substrate nanoantenna are almost perpendicular to each other. The preferred direction for the tip substrate is one along the line connecting the tip to the nearest particle of the substrate, or roughly perpendicular to the substrate plane. The apparatus may include means such as piezoelectric oscillators for oscillating the tip in a direction approximately perpendicular to the substrate plane at a selected frequency and include a lock-in amplifier to detect the Ramon signal at that oscillating frequency.

The metal particle constituting the metal of the tip or a metal coat layer on the tip of a dielectric or optical fiber can have a diameter in the 1–500 nm range to provide the highest possible resolution which is governed by the size of the tip. In another embodiment the tip may have a flat dielectric surface of up to 10 microns in diameter covered with periodic or quasi periodic metal particles in an array. The particle size and array spacing can be in the range 1–500 nm. An optical fiber tip 11 with metal coating can be cantilevered with an angle $\beta$ at the end, FIG. 3.

Our calculations support the statement that nanoantenna possesses wavelength, polarization selectivity, and ability to concentrate electromagnetic field in a nanoscale area. The results shown below emphasize the advantage of MTSN to control distance between nanoantenna parts and illustrate possible embodiment of the system.

It has been estimated [F. Brouers, S. Blacher, A. N. Lagarkov, A. K. Sarychev, P. Gadenne, V. M. Shalaev, Phys. Rev. B55, 13234 (1997)] that the enhancement of the Raman signal $G_R$, in comparison to the signal from the molecules on a dielectric substrate is $G_R \sim |\epsilon_m/\epsilon_d|^2 |I/I_0|^2$, where $I=|E(r)|^2$ is intensity of the local electric field, $I_0$ intensity of the impingent light, $\epsilon_m$ and $\epsilon_d$ are dielectric constants for the metal and dielectric substrates, correspondingly. Thus calculation of the $G_R$ reduces to calculation of the local field distribution $E(r)$ on the metal substrate below the tip.

Figure 4:
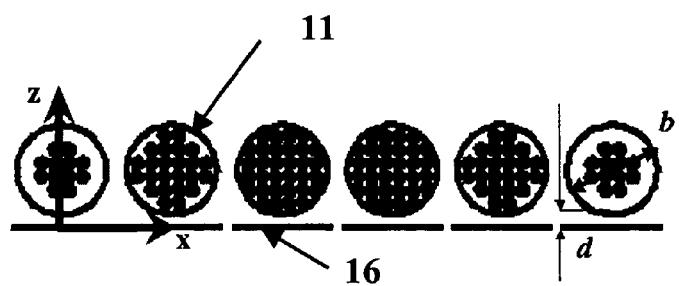
FIG. 4 shows a mutual sphere of diameter G at a distance above a metal surface. Six cross sections illustrate the approximation of the sphere by 136 dipoles.

We use a modified couple-dipole approach to calculate the local electric field between the tip and metallic substrate. In this approach the tip 11 is approximated by a collection of metal spheres (dipoles) whose size is much smaller than the size of the nanoantenna tip, FIG. 4. The electric field in the laser beam is assumed to be polarized perpendicular to the metal film 16. The nanoantenna is considered in the form of a spherical metal particle of diameter b at the end of the tip that is placed at the distance d above metal substrate. The spherical metal particle is approximated by dipoles. In FIG. 4 six cross sections illustrate the above metal approximation of the sphere by 136 dipoles.

Figure 5A:
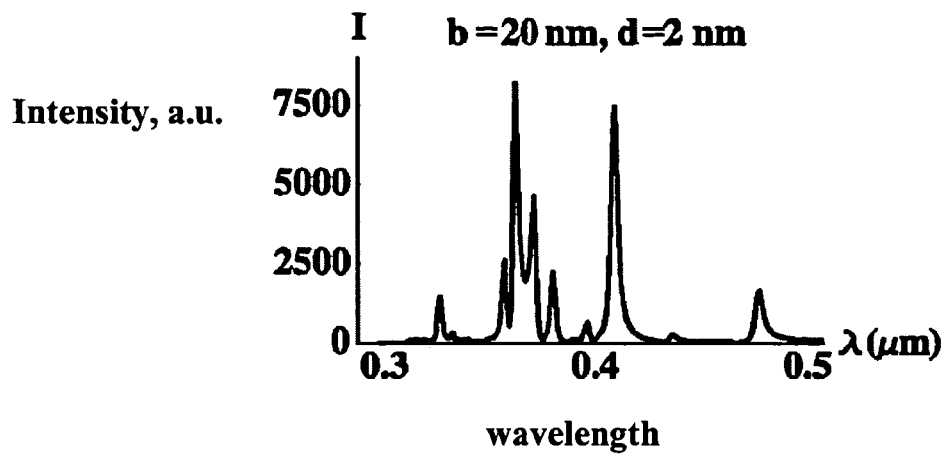
FIG. 5A–5C illustrate the wavelength dependence of local field interiority for different diameter spheres at different distances of the metal interface from the sphere.
Figure 5B:
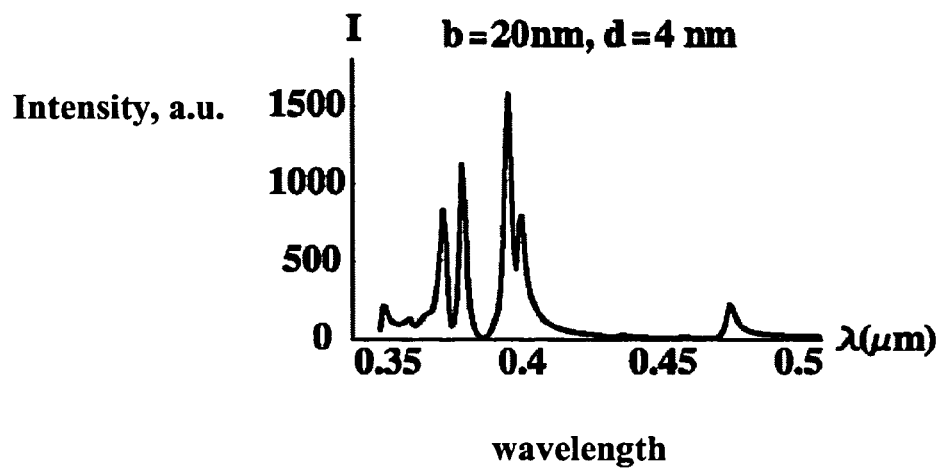
Figure 5C:
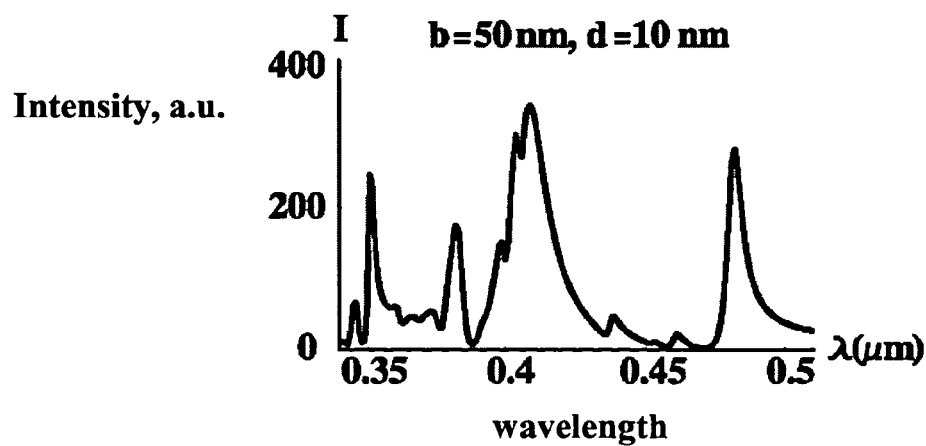

The wavelength dependencies of the local field intensity $I(r)$ on the metal substrate just below the nanoantenna tip is shown in FIGS. 5A, 5B and 5C as a function of the wavelength $\lambda$ of the laser light for different diameter b and distances d from the bottom of the spheres 11 to the metal film 16. In FIG. 5A b=20 nm and d=2 nm, in FIG. 5B b=20 nm and d=4 nm and in FIG. 5C b=50 nm and d=10 nm. The intensity $I(\lambda)$ of the local field has sharp resonances corresponding to the excitation of different surface plasmon modes in the system of metal tip+metal film.

Figure 6A:
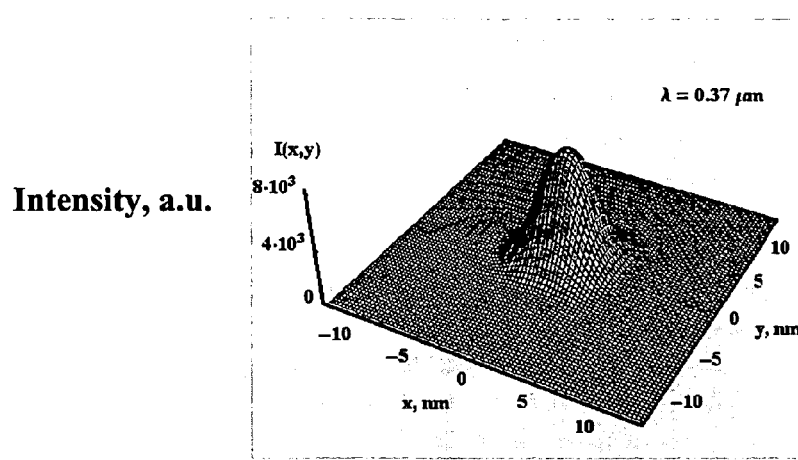
FIG. 6A–6C show the intensity of the local electric field at the metal inferface for a metal sphere of diameter d=2 nm at a distance b=20 nm from the metal interface.
Figure 6B:
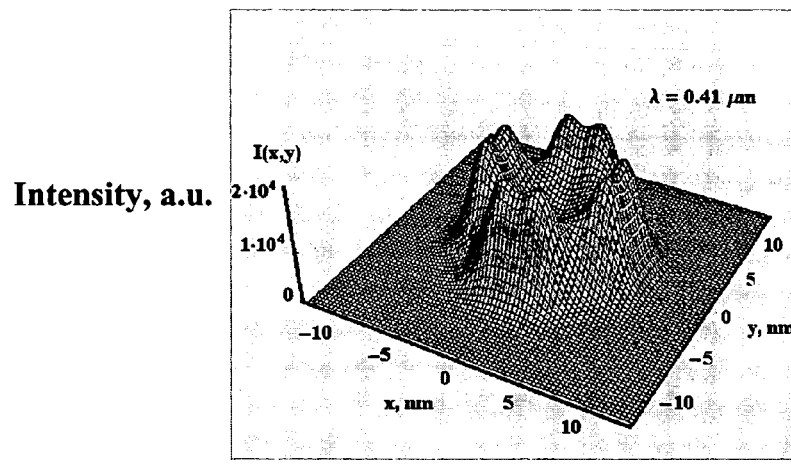
Figure 6C:
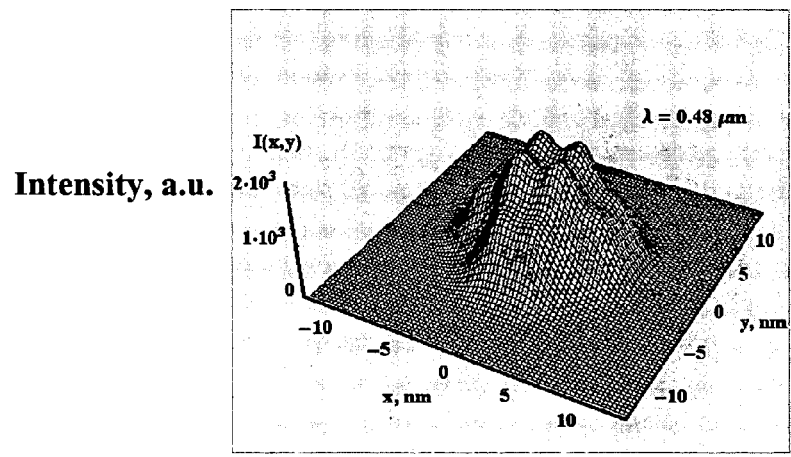
Figure 7A:
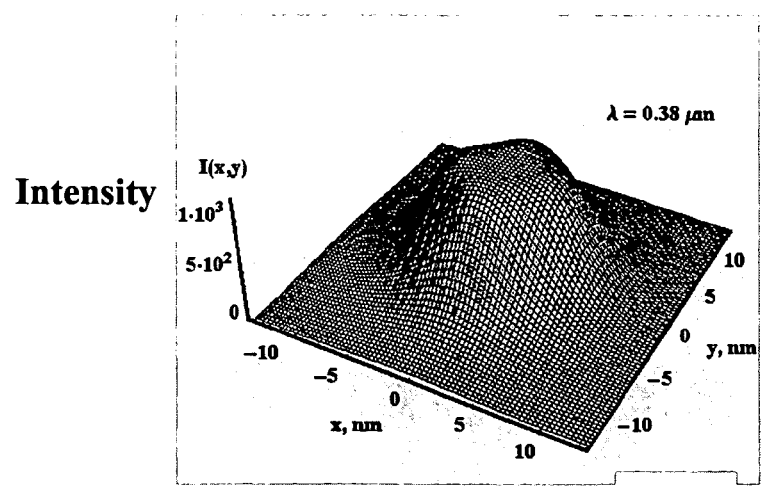
FIG. 7A–7C show the intensity of the local electric field at the metal inferface for a metal sphere of diameter d=4 nm at a distance b=20 nm from the metal interface.
Figure 7B:
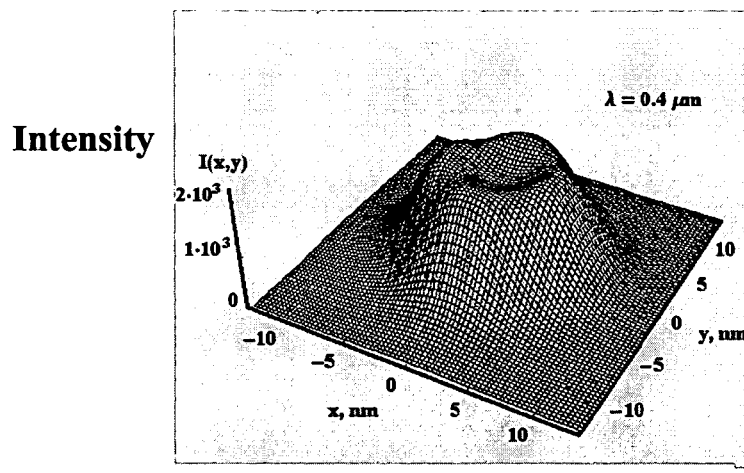
Figure 7C:
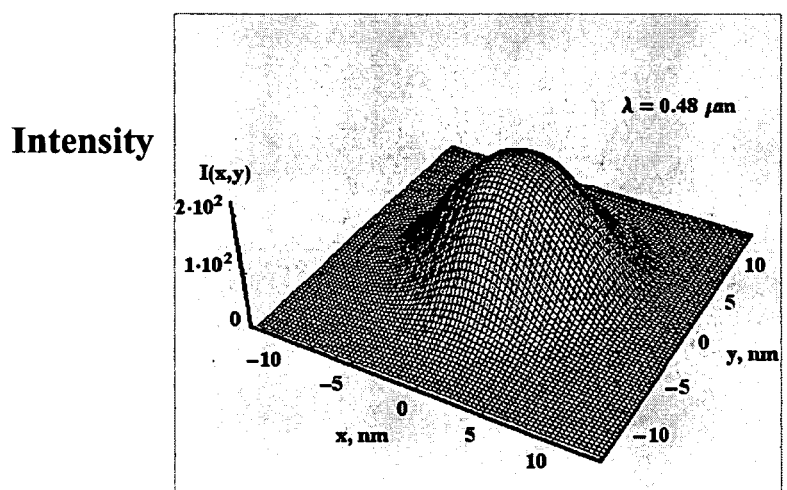
Figure 8A:
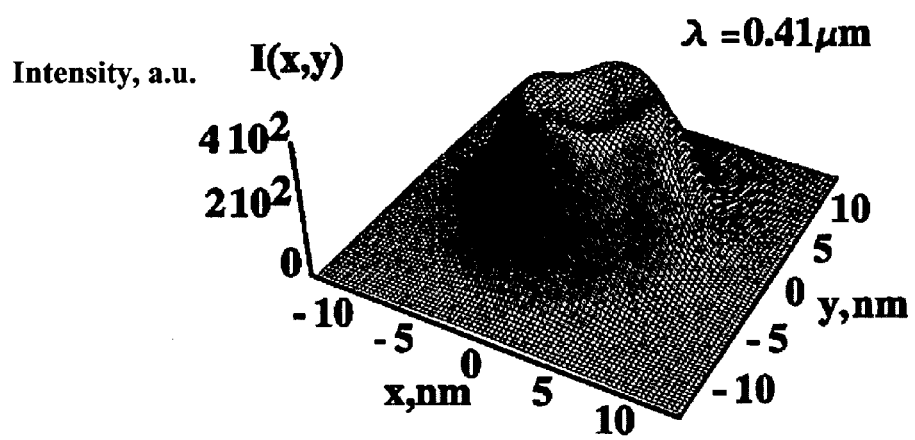
FIG. 8A–8B show the intensity of the local electric field at the metal inferface for a metal sphere of diameter d=10 nm at a distance b=50 nm from the metal interface
Figure 8B:
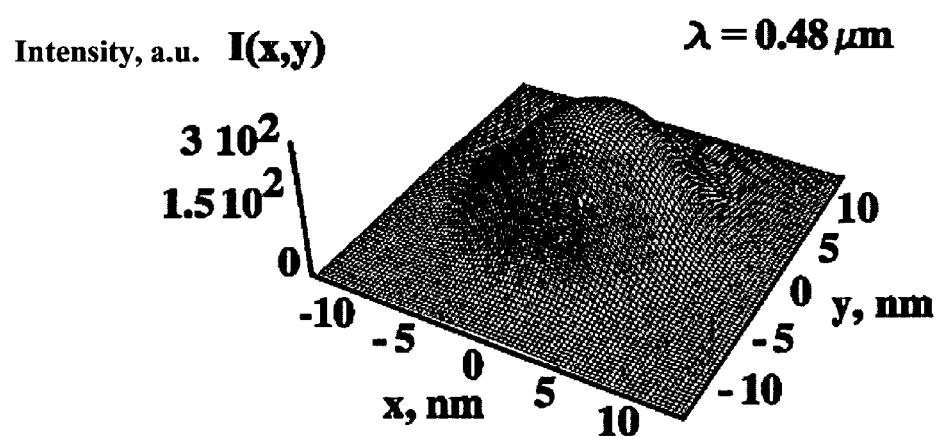

Spatial distribution of the intensity $I(x,y)=|E(x,y)|^2$ of the local electric field on the metal interface (plane z=0) is shown in FIGS. 6–8 for the same three spacings d and diameter b of FIGS. 5A–5C. FIGS. 6A–6C show the intensity of the local electric field at the metal interface (plane z=0) below the metal sphere of diameter b=20 nm; distance from the sphere to the metal interface d=2 nm for excitation light wavelength $\lambda$ equal to 0.37 $\mu$m, 0.41 $\mu$m, and 0.048 $\mu$m respectively. FIGS. 7A–7C show the intensity of the local electric field at the metal interface (plane z=0) below the metal sphere of diameter b=20 nm, distance from the sphere to the metal interface d=4 nm, for excitation light wavelength $\lambda$ equal to 0.38 $\mu$m, 0.4 $\mu$m and 0.48 $\mu$m respectively. FIGS. 8A and 8B show the intensity of the local electric field at the metal interface (plane z=0) below the metal sphere of diameter b=50 nm; distance from the sphere to the metal interface d=10 nm for excitation light wavelength $\lambda$ equal to 0.4 $\mu$m and 0.48$\mu$, respectively.

The local electric field strongly increases when the distance d between the metal particle and substrate decreases. FIGS. 6 and 7 show that the intensity I(x,y) increased by order of magnitude when the distance d decreases from 4 nm to 2 nm. Note that the distance between the center of the particle and the substrate changes by ~10% only when d decreases from 4 nm to 2 nm. Note that the spatial distribution of the local field is much more complicated than a single maximum picture predicted by one-dipole approximation. Thus in FIGS. 6B, 7B and 8A the intensity I(x,y) has a minimum at the point {x=0,y=0}, which corresponds to the minimal distance between particle and substrate surfaces.

The fine structure that appears in FIG. 6B–6C stems from the approximation of the metal particle by rather small number of dipoles. Yet, we believe that the discussed field minimum at {x=0,y=0} holds for the increasing numbers of the dipoles, approximated metal particle, since it is intrinsic feature of non-uniform plasmon resonance at wavelength $\lambda \approx 0.4$ μm.

FIGS. 7 and 8 also show that the enhancement of the local field is very sensitive to the absolute size of the nanoantenna. In both figures the ratio of the particle size b to the distance from the metal substrate is the same 20 nm/4 nm=5 and 50 nm/10 nm. Nevertheless the enhancement for the larger particles is about five times smaller for the main maxima at ($\lambda \approx 0.38, 0.4$ μm). This decreasing of the enhancement could be attributed to the radiative losses that become progressively important with increasing nanoantenna size or decreasing wavelength. Note that "longwave" maximum ($\lambda \approx 0.5$ μm) is less affected by the radiative losses.

In summary, there has been described a Raman imaging and sensing apparatus includes a metal tip which is spaced from a metal surface or particle to form therewith a nanoantenna and a light source for causing plasmon resonance between the metal tip and the spaced metal or particles. The metal tip-metal surface or particle interface provides enhanced Raman scattering. The apparatus can include a system such as that used in atomic force microscopes for precisely locating the tip relative to the surface or particles on the surface and for scanning the surface. A microscope such as a near field microscope can be used to receive the light scattered by the atoms, molecules, etc. (Raman scatter). A spectrophotometer provides a display of intensity as a function of wavelength for the molecules, atoms, ions, etc. which are vibrated by the plasmon resonance.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

What is claimed is:

1. Apparatus for exciting Raman scatter in a sample comprising:
   a nanoantenna formed by a metallic tip spaced from a metal surface, the metallic tip providing a condition for exclusive excitation of plasmon resonance at the tip position with insufficient excitation over the rest of the metal surface; and
   a light source for projecting a light beam onto the nanoantenna to cause plasmon resonance which excites the sample between the metallic tip and the metal surface coupled to the plasmon resonance to generate a characteristic enhanced Raman signal.

2. Apparatus for exciting Raman radiation as in claim 1 wherein the metal surface is a metallic film.

3. Apparatus for exciting Raman radiation as in claim 1 wherein the metal surface is a metallic particle or array of metallic particles.

4. Apparatus for exciting Raman radiation as in claims 1, 2 or 3 wherein the metallic tip is the pointed end of a metal probe.

5. Apparatus as in claims 1, 2 or 3 wherein the metallic tip comprises at least one metal particle at the end of a dielectric probe.

6. Apparatus as in claim 1, 2 or 3, wherein the metallic tip is a metal-coated fiber tip
   a light source for projecting a light beam onto said nanoantenna to cause plasmon reseonce to excite the sample between the maetallic tip and the metal surface and generate Raman scatter;
   Raman spectrophotometer for collecting the Raman spectrophotometer includes an optical microscope.

7. Apparatus for analyzing a sample comprising:
   a nanoantenna formed by a metallic tip spaced from a metal surface, the metallic tip providing a condition for exclusive excitation of plasmon resonance at the tip position with insufficient excitation over the rest of the metal surface;
   a light source for projecting a light beam onto said nanoantenna to cause plasmon resonance to excite the sample between the metallic tip and the metal surface and generate Raman scatter;
   a Raman spectrophotometer for collecting the Raman scatter and for providing an output characteristic of the sample.

8. Apparatus as in claim 7 in which the Raman spectrophotometer includes an optical microscope.

9. Apparatus as in claims 7 or 8 in which the metallic tip is positioned above the metal surface by an atomic force microscope mount.

10. Apparatus for analyzing samples carried at spaced locations on a substrate comprising:
    a nanoantenna formed by a probe with a metallic tip spaced from a metal surface on the substrate at said locations, the metallic tip providing a condition for exclusive excitation of plasmon resonance at the tip position with insufficient excitation over the rest of the metal surface;
    means for mounting the substrate and tip so that they can be moved relative to each other in the x, y and z directions to scan the surface of the substrate and to control the spacing of the metallic tip relative to the metal surface whereby the probe sequentially cooperates with a sample at each of said spaced locations;
    a light source for projecting a light beam onto said nanoantenna at each of said locations to cause plasmon resonance which excites the sample at said locations to cause the sample to vibrate and generate Raman scatter; and
    a Raman spectrophotometer for collecting the Raman scatter and providing an output characteristic of the sample.

11. Apparatus as in claim 10 in which the tip is maintained at a spacing of between 1 nm and 100 nm.

12. Apparatus as in claims 10 or 11 in which the diameter of the metallic tip is between 51 nm and 500 nm.

13. Apparatus as in claim 10 in which the tip is maintained at a height of between 2 nm and 10 nm.

14. Apparatus as in claims 10 or 11 in which the diameter of the metallic tip is between 20 nm and 50 nm.

15. Apparatus as in claim 10 in which the metal surface is a metal film.

16. Apparatus as in claim 10 in which the metal surface comprises an array of metal particles.

17. Apparatus as in claim 9 in which the metallic tip is cantilevered with respect to the atomic force microscope mount.

18. Apparatus as in claim 10 in which the metallic tip is cantilevered with respect to the mounting means for the tip.

19. Apparatus for exciting Raman scatter in a sample comprising:
- a nanoantenna formed by a metal-coated fiber tip spaced from a metal; and
- a light source for projecting a light beam onto the nanoantenna to cause plasmon resonance which excites the sample coupled to the plasmon resonance to generate a characteristic enhanced Raman signal.

20. Apparatus for analyzing a sample comprising:
- a nanoantenna formed by a metal-coated fiber tip spaced from a metal surface or particle;
- a light source for projecting a light beam onto said nanoantenna to cause plasmon resonance to excite the sample and generate Raman scatter;
- a Raman spectrophotometer for collecting the Raman scatter and for providing an output characteristic of the sample.

21. Apparatus for analyzing samples carried at spaced locations on a substrate comprising:
- a nanoantenna formed by a probe with a metal-coated fiber tip spaced from metal on the substrate at said locations;
- means for mounting the substrate and tip so that they can be moved relative to each other in the x, y and z directions to scan the surface of the substrate and to control the spacing of the metal-coated fiber tip relative to the metal whereby the probe sequentially cooperates with sample at each of said spaced locations;
- a light source for projecting a light beam onto said nanoantenna at each of said locations to cause plasmon resonance which excites the sample at said locations to cause sample to vibrate and generate Raman scatter; and
- a Raman spectrophotometer for collecting the Raman scatter and providing an output characteristic of the sample.

* * * * *

UNITED STATES PATENT AND TRADEMARK OFFICE
CERTIFICATE OF CORRECTION

PATENT NO. : 6,985,223 B2
DATED : January 10, 2006
INVENTOR(S) : Vladimir P. Drachev et al.

It is certified that error appears in the above-identified patent and that said Letters Patent is hereby corrected as shown below:

<u>Column 8,</u>
Lines 19-24, delete the following:
"a light source for projecting a light beam onto said nanoantenna to cause plasmon reseonce to excite the sample between the maetallic tip and the metal surface and generate Raman scatter;
Raman spectrophotometer for collecting the Raman spectrophotometer includes an optical microscope."

Signed and Sealed this

Eleventh Day of April, 2006

JON W. DUDAS
*Director of the United States Patent and Trademark Office*